US007687652B2

(12) United States Patent
Rochlin et al.

(10) Patent No.: US 7,687,652 B2
(45) Date of Patent: Mar. 30, 2010

(54) SPHINGOMYELIN, INTERMEDIATES THEREOF AND METHODS FOR PREPARATION OF SAME

(75) Inventors: Elimelech Rochlin, Jerusalem (IL); Jean Hildesheim, Mazkeret Batya (IL); Alisa Berlin, Jerusalem (IL)

(73) Assignee: Biolab Ltd, Jerusalem (IL)

( * ) Notice: Subject to any disclaimer, the term of this patent is extended or adjusted under 35 U.S.C. 154(b) by 0 days.

(21) Appl. No.: 10/586,056

(22) PCT Filed: Jan. 13, 2005

(86) PCT No.: PCT/IL2005/000043

§ 371 (c)(1),
(2), (4) Date: Jun. 11, 2007

(87) PCT Pub. No.: WO2005/068480

PCT Pub. Date: Jul. 28, 2005

(65) Prior Publication Data

US 2007/0282120 A1    Dec. 6, 2007

Related U.S. Application Data

(60) Provisional application No. 60/536,507, filed on Jan. 15, 2004.

(51) Int. Cl.
*C07F 9/02*    (2006.01)
(52) U.S. Cl. ...................... 556/405; 558/169
(58) Field of Classification Search ............ 556/405; 558/169
See application file for complete search history.

(56) References Cited

U.S. PATENT DOCUMENTS 5,220,043 A    6/1993    Dong et al.

FOREIGN PATENT DOCUMENTS

| JP | 2003 137894 A2 | 5/2003 |
| JP | 2004 002215 A | 1/2004 |
| WO | WO 93/19760 A1 | 10/1993 |
| WO | WO 95/21848 A1 | 8/1995 |
| WO | WO 99/41266 A1 | 8/1999 |

OTHER PUBLICATIONS

Deigner et al., Rapid synthesis of 2-desoxy-2-amino-3-phosphocholine-glycerinic-acid-alkylester, 1-alkyl-I-desoxy- and 1-o-alkyl-2-desoxy-2-amino-sn-glycero-3-phosphocholines,-3-phospho-N,N'-dimethylethanolamine and-3-phospho-Fmoc-serine-methylester, Chemistry and Physics of Lipids, vol. 61, 1992, pp. 199-208.*
Deigner et al., Synthesis of [32P] labelled 1-O-alkyl-2-desoxy-2-amino-sn-glycero-3-phosphocholines, Journal of Labelled Compounds and Radiopharmceuticals, vol. 34, No. 2, 1994, pp. 185-190.*
Lorene et al., Synthesis of N-Lost derivatives. II. Reaction of N,N-bis(2-chloroethyl)phosphoramidic dichloride with 1-aminopropane-2,3-diol, Archiv Der Pharmazie (Weinheim, Germany) , 319(11), 1023-7, 1986.*
Deigner et al., Synthesis of [32P] labelled 1-O-alkyl-2-desoxy-2-amino-SN-glycero-3-phosphocholines, Journal of Labelled Compounds and Radiopharmceuticals, vol. 34, No. 2, 1994, pp. 185-190.*
Deigner et al., {Rapid synthesis of 2-desoxy-2-amino-3-phosphocholine-glycerinic-acid-alkylester, 1-alkyl-I-desoxy- and 1-o-alkyl-2-desoxy-2-amino-sn-glycero-3-phosphocholines,-3-phospho-N,N'-dimethylethanolamine and-3-phospho-Fmoc-serine-methylester, Chemistry and Physics of Lipids, vol. 61, 1992, pp. 199-208.*
Lorene et al., Synthesis of N-Lost derivatives. II. Reaction of N,N-bis(2-chloroethyl) phosphoramidic dichloride with 1-aminopropane-2,3-diol, Archiv Der Pharmazie (Weinheim, Germany) , 319(11), 1023-7, 1986.*
Lorene et al., {Synthesis of N-Lost derivatives. II. Reaction of N,N-bis(2-chloroethyl) phosphoramidic dichloride with 1-aminopropane-2,3-diol, Archiv Der Pharmazie (Weinheim, Germany) , 319(11), 1023-7, 1986}.*
Deigner et al., (2) {Rapid synthesis of 2-desoxy-2-amino-3-phosphocholine-glycerinic-acid-alkylester, 1-alkyl-I-desoxy- and 1-o-alkyl-2-desoxy-2-amino-sn-glycero-3-phosphocholines,-3-phospho-N,N'-dimethylethanolamine and-3-phospho-Fmoc-serine-methylester, Chemistry and Physics of Lipids, vol. 61, 1992, pp. 199-208}.*
Deigner et al., {Synthesis of [32P] labelled 1-O-alkyl-2-desoxy-2-amino-SN-glycero-3-phosphocholines, Journal of Labelled Compounds and Radiopharmceuticals, vol. 34, No. 2, 1994, pp. 185-190}.*
Lorenz, Peter et al., "Synthesis of N-Lost derivatives. II. Reaction of N-bis(2-chloroethyl)phosphoramidic dichloride with 1-Aminopropane-2,3-diol," Archiv der Pharmazie, 1986, pp. 1023-1027, vol. 319 (11), VCH Verlagsgesellschaft mbH, Weinheim, Germany.
Ramstedt, Bodil et al., "Comparison of the Biophysical Properties of Racemic and d-Erythro-N-Acyl Sphingomyelins," Biophysical Journal, Sep. 1999, pp. 1498-1506, vol. 77 (3), Biophysical Society.
Kratzer, Bernd et al., "Efficient Synthesis of Sphingosine-1-phosphate, Ceramide-1-phosphate, Lysosphingomyelin, and Sphingomyelin," Liebigs Annalen, 1995, pp. 957-963, VCH Verlagsgesellschaft mbH, Weinheim, Germany.
Zanglis, Anthony et al., "The Biological Activity of Acetylated Sphingosylphosphorylcholine Derivatives," International Jounal of Biochemistry & Cell Biology, 1996, pp. 63-74, vol. 28 (1), Elsevier Science Ltd., Great Britain.

(Continued)

*Primary Examiner*—Daniel M Sullivan
*Assistant Examiner*—Chukwuma O Nwaonicha
(74) *Attorney, Agent, or Firm*—The Nath Law Group; Susanne M. Hopkins; Ari G. Zytcer

(57)    ABSTRACT

Novel cyclic and acyclic oxazaphospholanes are described, as well as their use in the synthesis of sphingomyelin and sphingomyelin analogous. The production of synthetic sphingomyelins is also described. 2S, 3R stereoisomers of oxazaphospholanes and sphingomyelins, and synthetic methods for their preparation are described.

24 Claims, No Drawings

OTHER PUBLICATIONS

Thompson, Charles M. et al., "Synthesis, Configuration, and Chemical Shift Correlations of Chiral 1,3,2-oxazaphospholidin-2-ones derived from I-Serine," Journal of Organic Chemistry, 1990, pp. 111-116, vol. 55, American Chemical Society.

He, Zheng-Jie et al., "Synthesis of Novel Optically Active Cyclic Phospholipid Conjugates of Tegafur and Uridine starting from L-serine," Phosphorous, Sulfur and Silicon, 2000, pp. 223-232, vol. 160, Overseas Publishers Association Amsterdam N.V., Malaysia.

Bruzik, Karol S., "Synthesis and Spectral Properties of Chemically and Stereochemically Homogenous Sphingomyelin and its Analogues," Journal of the Chemical Society Perkin Transactions 1, 1988, pp. 423-431.

Do, Un Hoi et al., "Mild Alkali-stable Phospholipids in Chicken Egg Yolks: Characterization of 1-Alkenyl and 1-Alkyl-SN-Glycero-3-Phosphoethanolamine, Sphingomyelin, and 1-Alkyl-SN-Glycero-3-Phosphocholine," Journal of Lipid Research, 1980, pp. 888-894, vol. 21.

Martin, M.-J. et al., "Distribution of Bovine Milk Sialoglycoconjugates During Lactation," Journal of Dairy Science, 2001, pp. 995-1000, vol. 84, American Dairy Science Association.

Martin, María-Jesús. et al., "Bovine Milk Gangliosides: Changes in Ceramide Moiety with Stage of Lactation," Lipids, 2001, pp. 291-298, vol. 36 (3), AOCS Press.

Benda, P. et al., "Testing of TKT Medium for *Streptococcus agalactiae* Screening in Bulk Milk Samples," Vet. Med.-Czech., 1997, pp. 71-80, vol. 42 (3).

Barenholz, Yechezkel et al., "Sphingomyelin: Biophysical Aspects," Chemistry and Physics of Lipids, 1999, pp. 29-34, vol. 102.

Barenholz, Y. et al., "Sphingomyelins in Bilayers and Biological Membranes," Biochimica et Biophysica Acta, 1980, pp. 129-158, vol. 604, Elsevier/North-Holland Biomedical Press.

Barenholz, Y. et al., "A Calorimetric Study of the Thermotropic Behavior of Aqueous Dispersions of Natural and Synthetic Sphingomyelins," Biochemistry, 1976, pp. 2441-2447, vol. 15 (11).

Eckhardt, Erik R.M. et al., "Dietary Sphingomyelin Suppresses Intestinal Cholesterol Absorption by Decreasing Thermodynamic Activity of Cholesterol Monomers," Gastroenterology, 2002, pp. 948-956, vol. 122, American Gastroenterological Association.

Morrison, W.R. et al., "Polar Lipids in Bovine Milk: II. Long-chain Bases, Normal and 2-Hydroxy Fatty Acids, and Isomeric CIS and TRANS Monoenoic Fatty Acids in the Sphingolipids," Biochimica et Biophysica Acta, 1970, pp. 460-467, vol. 202.

Greene, T.W. et al., Protective Groups in Organic Synthesis, Second Edition, 1980, John Wiley & Sons, Inc.

* cited by examiner

SPHINGOMYELIN, INTERMEDIATES THEREOF AND METHODS FOR PREPARATION OF SAME

CROSS-REFERENCE

This is a National Phase Application filed under 35 U.S.C. 371 of International Application No. PCT/IL2005/000043, filed Jan. 13, 2005, claiming the benefit under 35 USC 119(e) of U.S. Provisional Application No. 60/536,507, the entire contents of each of which is hereby incorporated herein by reference in its entirety.

FIELD OF THE INVENTION

The invention relates to novel phospholipids, in particular to oxazaphospholanes which are intermediates, inter alia, in the process for preparing sphingomyelin and sphingomyelin analogous.

PRIOR ART

The following is the prior art which is considered to be pertinent for describing the state of the art in the field of the invention.
Bruzik, K. S. *J. Chem. Soc., Perkin Trans.* 1: 423-431, 1988
U.S. Pat. No. 5,220,043

BACKGROUND OF THE INVENTION

In recent years, phosphosphingolipids such as sphingomyelins (SPMs) are gaining interest for pharmaceutical and therapeutic applications.

Sphingolipids and especially SPMs are unique in their chemical stability. Lacking ester bonds and polyunsaturated acyl chains they resist hydrolysis and oxidation during storage and formulation processing. Therefore, SPMs are excellent candidates for drug delivery formulations based on liposomes and other lipid assemblies. Having full control over the composition one can design SPMS which, when present in a lipid bilayer under physiological conditions (e.g. at body temperature) may be in a fluid (i.e., N-oleoyl sphingomyelin), or solid (i.e., N-stearoyl sphingomyelin) state, or design SPMs which enable the generation of thermo-sensitive liposomes.

Another unique feature of SPMs is their high affinity for cholesterol thereby serving as potential drug to induce reverse cholesterol transport in cardiovascular diseases.

Initially, SPMs were obtained by extraction of animal tissue and further purification. But in the last two decades several synthetic strategies have been suggested to prepare SPM and related compounds.

When synthesized correctly, a sphingomyelin is a single molecular species composed of only one sphingoid base of a D-erythro configuration and one acyl chain (e.g. D-erythro N-palmitoyl sphingomyelin). Such SPMs are mainly obtained from milk or egg yolk and are present therein at very low concentrations. As a result, the extract is typically contaminated with other lipids, such as 1-alkyl-sn-glycerophoshoethanol amine and 1 alkyl-sn-glycerol phosphocholine [Do, U. H. and Ramochardarn, S. (1980) *J. Lipid Res.* 21, 888-894].

In addition, the extract may contain lipid contaminants which are resistant to known purification procedures. For example, milk derived lipids include a mixture of SPMs such as neutral glycosphingolipids and gangliosides [Martin, M. J., et al. (2001) *J. Dairy Sci.* 84, 995-1000; Martin, M. J., et al. (2001) *Lipids* 36, 291-298], being resistant to alkaline hydrolysis and thus glycosphingolipids may contaminate milk-derived sphingomyelin. As appreciated by those versed in the art, glycosphingolipids, like peptides and proteins, may be immunogenic and thus their present in the extract is not preferable.

There are also reports that lipids derived of milk (including milk derived sphingomyelin) may be contaminated with bacterial products such as from *Streptococcus agalacial* [Bendle, P. and Vuyletelova, M. (1997) *Vet. Med.* 42, 71-80].

In addition, milk-derived SPM and egg-derived SPM are known to include mixtures of SPMs which vary in their acyl chains [see for example Avanti Polar Lipids Inc. Products Catalog Edition VI, p. 58]. Typically, milk-derived SPMs are enriched with C24:0>C18:1>C16:0>>C18:0 and contain many other acyl chains. The very high percentage of these long acyl chains and therefore large mismatch between the two hydrocarbon chains makes this SPM very different from the egg-derived SPMs. The level of chain mismatch is a very important parameter in determining the physicochemical properties of SPMs [rev. in Barenholz, Y. and Thompson, T. E. (1999) *Chem. Phys. Lipids* 102, 29-34; Barenholz, Y. and Thompson, T. E. (1980) *Biochim. Biophys. Acta* 604, 129-158; Barenholz et al. (1976) *Biochemistry* 15, 2441-2447]. A major difference in the ability of the two SPMs to suppress intestinal cholesterol absorption by decreasing thermodynamic activity of cholesterol monomers was recently observed [Eckhardt, E. R., et al. W (2002) *Gastroenterology* 122, 948-956]. In addition, the SPMs derived of natural sources have more than one sphingoid base. Although C18 D-erythro sphingosine is the main sphingoid base, other sphingoid bases accompany the main base in significant percentage. Especially the sphingoid base dihydrosphingosine (which is saturated and lacks the trans double bond between C4-C5), and smaller amounts of sphingosine and dihyrosphingosine bases other than C18 [Morrison, W. R. and Hay, J. D. (1970) *Biochim. Biophys. Acta* 202, 460-467]. Both egg yolk derived SPM and milk-derived SPM sphingoid base and acyl chain composition is affected by diet and therefore batch to batch variation in sphingoid and acyl chain composition may occur and should be carefully studied. Such changes may also be reflected in the physicochemical and biological properties of the different batches.

SUMMARY OF INVENTION

The present invention is based on the novel development of a single pot procedure for the manufacture of sphingomyelin derivatives and intermediates thereof from a sphingoid. It has been surprisingly found that one intermediate in the process is a cyclic oxazaphospholane compound of the following formula (1), as defined hereinafter. This cyclic oxazaphospholane compound was isolated and found to be stable.

Thus, according to a first aspect the present invention provides an oxazaphospholane compound of the following formula (1):

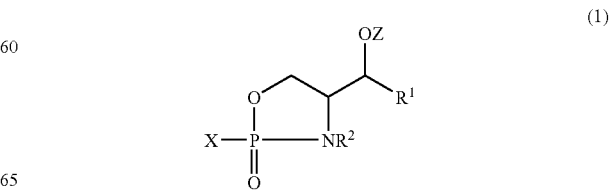

wherein $R^1$ and $R^2$ represent a hydrophobic group, $R^2$ also represents a hydrogen atom, Z represents a protecting group and X represents a leaving group, all of which are as further defined hereinafter. This compound, more particularly, the 2S, 3R stereoisomer thereof was isolated and characterized as a stable intermediate in the process of preparing sphingomyelin derivatives and precursors thereof from a sphingoid as a starting material.

In the following description whenever a reference number for a compound is suffixed with the letter 'a' it denotes the 2R, 3S stereoisomer of the referenced compound. For example, compound (1a) refers to the 2S, 3R stereoisomer of compound (1).

The invention also provides a process for the manufacture of an oxazaphospholane compound of formula (1) or its 2S, 3R stereoisomer (1a), the process comprises reacting a phosphorylating reagent with a 3-O-protected sphingoid compound of the following formula (2):

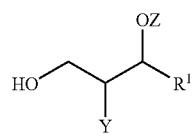

(2)

wherein $R^1$, Z and X are as defined and Y is an amine or amino group (i.e. any amine or amino containing group).

Evidently, any oxazaphospholane compound of formula (1) or (1a) obtainable by the above process forms part of the invention.

The invention also concerns the use of the oxazaphospholane compound of formula (1) or (1a) either as an isolated starting material, or as crude material obtained from the sphingoid compound of formula (2), for the preparation of several significant sphingomyelin intermediates.

According to one aspect of the invention, there is provided a process making use of the oxazaphospholane compound of formula (1) or (1a), for the preparation of an acyclic oxazaphospholane having the following formula (3):

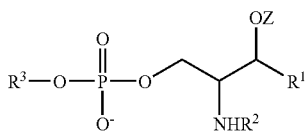

(3)

or its 2S, 3R stereoisomer (3a), wherein $R^1$, $R^2$ and Z are as defined, and $R^3$ represent a hydrogen atom. an aliphatic moiety selected from aliphatic chain, amino aliphatic chain, heteroatom comprising aliphatic chain, aliphatic chain comprising a cyclic ring which ring may be saturated, partially saturated ring or an aryl group, said aliphatic chain may be branched or straight, saturated or unsaturated chain; or ether, polyether or sugar moiety; the process comprises the step of reacting said oxazaphospholane of formula (1) with an alcohol of the formula $R^3OH$ where $R^3$ is as defined, in the presence of an aqueous base or an aqueous acid.

According to another embodiment of the invention, there is provided a process making use of the oxazaphospholane of formula (1) or (1a) wherein $R^1$, and Z are as defined and $R^2$ is a hydrogen atom, for the manufacture of an acyclic oxazaphospholane derivative having the following formula (4):

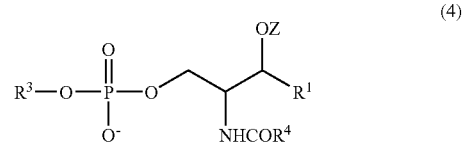

(4)

or its 2S, 3R stereoisomer (4a) wherein $R^3$ represent a hydrogen atom; an aliphatic moiety selected from aliphatic chain, amino aliphatic chain, heteroatom comprising aliphatic chain, aliphatic chain comprising a cyclic ring which ring may be saturated, partially saturated or aromatic ring, said aliphatic chain may be branched or straight, saturated or unsaturated chain; or ether, polyether or sugar moiety; and $R^4$ represents a hydrophobic group;

the process comprises preparing an oxazaphospholane of formula (3) and reacting the oxazaphospholane of formula (3) with an acyl compound of formula $R^4C(O)Q$, wherein Q is a leaving group, which may be the same or different from X.

According to yet another embodiment of the invention there is provided a process making use of the oxazaphospholane of formula (1) wherein $R^1$, and Z are as defined and $R^2$ is a hydrogen atom, for the manufacture of a sphingomyelin derivative having the following formula (5):

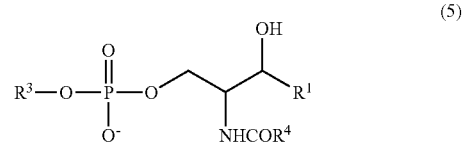

(5)

or its 2S, 3R stereoisomer (5a), wherein $R^3$ and $R^4$ are as defined; the process comprises preparing an oxazaphospholane of formula (4) as defined and reacting said oxazaphospholane of formula (4) with protecting group removing agent to obtain a said sphingomyelin.

Evidently, the invention provides any sphingomyelin analogue (5) or intermediate thereof having the general formulae (3) and (4) obtainable by the sequence processes of the invention, preferably, those obtained by the sequence of processes of the present invention.

In accordance with the invention there is also provided a process making use of the oxazaphospholane of formula (1) of the invention for the manufacture of an acyclic oxazaphospholane having the following formula (6):

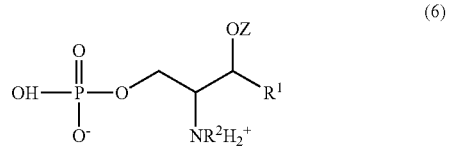

(6)

or its 2S, 3R stereoisomer (6a), wherein $R^1$, $R^2$ and Z are as defined, the process comprises reacting said oxazaphospholane of formula (1) with an aqueous base or an aqueous acid. The acyclic oxazaphospholane having the following formula (6) also forms part of the invention.

Finally, the invention concerns the use of sphingomyelin and sphingomyelin analogous obtainable by the above disclosed sequence of synthetic reaction in the preparation of pharmaceutical compositions and such therapeutic compositions per se.

DETAILED DESCRIPTION AND SPECIFIC EMBODIMENTS

In the following description reference numbers are used in brackets to denote a specific general formula. For example, in the following description sphingomyelin (5) denotes a sphingomyelin of the general formula (5) as defined hereinbelow.

As appreciated, numerous attempts have been made to develop synthetic routes for the production of sphingomyelin (5a) and its analogs:

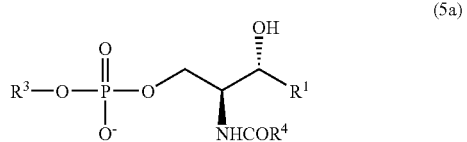

(5a)

$R^1$, $R^4$ representing a hydrophobic group (which may be the same or different), and $R^3$ representing any one of a hydrogen atom; an aliphatic moiety selected from aliphatic chain, amino aliphatic chain, heteroatom comprising aliphatic chain, aliphatic chain comprising a cyclic ring which ring may be saturated, partially saturated ring or an aryl group, said aliphatic chain may be branched or straight, saturated or unsaturated chain; or ether, polyether or sugar moiety.

Currently SPMs may be obtained from natural sources or synthetically in small scale production. The synthetic approaches exerted by different groups vary mainly by the strategy of introducing the phosphate moiety into the ceramide backbone. Most of the procedures are multistep procedures, which require isolation and purification of the intermediates (typically by column chromatography). The procedures described in the art use appropriately substituted phosphoryl chlorides or phosphoramidites as phosphorylation reagents.

One procedure described by Brunzik et al. [Bruzik, K. S. 1988. *J. Chem. Soc., Perkin Trans.* 1: 423-431] exhibits a one-pot procedure, however, the reagents employed, phosphoramidites, are rather expensive, extremely sensitive to the reaction and storage conditions and hence are considered inconvenient for scaling up of SPM production.

The present invention is based on the surprising finding that an inexpensive and widely available reagent $POCl_3$, which is extensively utilized for several decades in phospholipids synthesis, is suitable for the production of different Sphingolipids in a single pot process. This single pot process may be easily utilized for large scale production of any of the Sphingolipids detailed herein. As used herein the term "single pot process" denotes that in a sequence of synthesis reactions there is no need for the isolation and purification (even partial purification) of intermediates obtained by each chemical reaction step, until the synthesis of the product at the end of the sequence. Nonetheless, it should be understood that if desired, each intermediate product in the sequence of synthesis reactions may as well be isolated and purified and thus used for other purposes.

It has now been found that oxazaphospholane (1), sphingomyelin (5), sphingosine-1-phosphate (7) lysosphingomyelin (8) and their 2S, 3R stereoisomer as well as their chemical analogs and precursors may be prepared by an economically feasible procedure, making use of widely available phosphorylation reagents.

In accordance with the invention, there is thus provided an oxazaphospholane (1) and its 2S, 3R stereoisomer (1a).

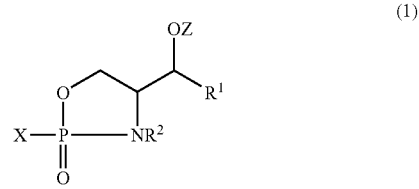

(1)

wherein $R^1$ represents a hydrophobic group and $R^2$ represent a hydrogen atom or a hydrophobic group, Z represents a protecting group and X represents a leaving group.

According to one embodiment, $R^1$ represents a $C_1$-$C_{24}$ aliphatic moiety which may be saturated or unsaturated, branched or linear chain, optionally containing an aliphatic ring; and $R^2$ represents a hydrogen atom or a $C_1$-$C_{24}$ aliphatic moiety selected from saturated or unsaturated, branched or linear aliphatic chain, said aliphatic chain optionally containing an aliphatic ring; the aliphatic chain or ring optionally substituted with one or more substituents containing a heteroatom selected from oxygen, halogen, nitrogen and sulfur.

More specifically, the invention concerns an oxazaphospholane compound wherein said $R^1$ represents a $C_8$-$C_{24}$ aliphatic moiety.

Further, more specifically, the invention concerns an oxazaphospholane wherein said $R^2$ represents a hydrogen atom or a saturated or unsaturated $C_8$-$C_{24}$ aliphatic moiety, however, preferably a hydrogen atom.

According to the invention, X is a leaving group. The term "leaving group" as used herein in connection with the substituent X or Q (hereinbelow) denotes any chemical moiety which in the presence of a nucleophilic reagent is replaced by the nucleophile. Under these conditions it is to be understood that X also denotes the nucleophilic moiety after substituting the leaving group (as a result of the nucleophilic attack).

Non-limiting examples of a leaving group (X or Q, the latter referred to hereinbelow) include a halogen atom, borate, ethylene chlorophosphite, methyl phosphodichloridite, chloro-N,N-diisopropylaminomethyxophosphite or [(isopropyl)$_2$N]$_2$POCH$_2$CH$_2$CN.

According to one embodiment, X represents a halogen, preferably Cl.

According to another embodiment, X is substituted (preferably as a result of a substitution reaction) with a group selected from an alcohol containing an aliphatic moiety selected from aliphatic chain, amino aliphatic chain, heteroatom comprising aliphatic chain, aliphatic chain comprising a cyclic ring which ring may be saturated, partially saturated ring or an aryl group, said aliphatic chain may be branched or straight, saturated or unsaturated chain; or ether, polyether, or sugar moiety. According to one embodiment, X is —O—CH$_2$—CH$_2$—N$^+$(CH$_3$)$_3$.

According to the invention preferred Z protecting groups are, without being limited thereto, methoxymethyl (MOM), tetrahydropyranyl (THP), diphenylmethyl, triethylsilyl (TES), t-butyldimethylsilyl (TBDMS), mesitoate, 9-fluorenylmethyl carbonate (f-moc), t-butyl carbamate (t-boc).

According to one embodiment Z represents a compound Si(R$^5$)$_3$ wherein R$^5$ may be the same or different in the same moiety and represent a $C_1$-$C_6$ branched or straight alkyl group or an aryl group. It should be understood that aryl includes a substituted as well as non-substituted aromatic ring. A preferred Z group is $Si(Ph)_2(t-Bu)$.

A specific embodiment of the concerns the 2S, 3R stereoisomer (1a):

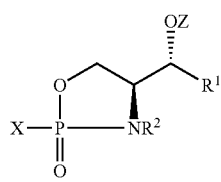
(1a)

with $R^1$, $R^2$, X and Z being as defined above.

A specific example of oxazaphospholane (1) is that in which $R^1$ is (E)-CH=$CHC_{13}H_{27}$, $R^2$ is hydrogen, X is Cl and Z is $Si(Ph)_2(t-Bu)$, having the formula (1b).

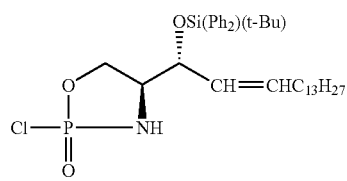
(1b)

The structure of this compound (1b) was verified by observing the specific molecular peak in the mass spectrum (detailed below).

Another specific example of oxazaphospholane (1) is that in which $R^1$ is (E)-CH=$CHC_{13}H_{27}$, $R^2$ is hydrogen, X is substituted with the group —O—$CH_2$—$CH_2$—$N^+(CH_3)_3$.

As stated hereinabove, a unique finding of the present invention is that the oxazaphospholane (1) or (1a) may be isolated and is substantially stable.

The invention also concerns a process for the manufacture of the oxazaphospholane (1), (1a) or (1b). According to the invention, the process comprises reacting with a phosphorylating reagent with a 3-O-protected sphingoid compound of the following formula (2):

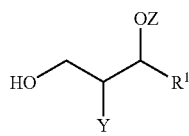
(2)

wherein $R^1$, Z and X are as defined and Y is an amine or an amino group. The term "amino group" denotes any amine containing moiety known in the art, including alkylamine (saturated as well as unsaturated, branched or straight), amino alcohols, arylamines, aminothiols, amino sugars etc. According to one embodiment, Y represents $NH_2$.

In order to obtain the 2S, 3R stereoisomer, the starting material in the above process is the sphingoid compound of the following formula (2a):

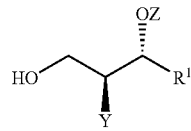
(2a)

The term "phosphorylating reagent" denotes any reagent having a reactive P=O moiety which may be reacted with the hydroxyl and Y group of compound (2) so as to form a cyclic oxazaphospholane (1). Non-limiting examples of a phosphorylating reagent include a compound having the general formula $POW_3$, in which W represents a halogen atom, borate, ethylene chlorophosphite, methyl phosphodichloridite, chloro-N,N-diisopropylaminomethyxophosphite or [(isopropyl)$_2$N]$_2$POCH$_2$CH$_2$CN.

A preferred phosphorylating reagent is $POCl_3$.

Evidently, the invention concerns any oxazaphospholane (1) as well as its stereoisomers, whenever prepared by the process of the invention, as well as by any other process.

It should be appreciated that oxazaphospholane (1) may be utilized in various applications and processes, including as a starting (or intermediate) material in the preparation of oxazaphospholane derivatives, sphingomyelin and sphingomyelin derivatives. While the following processes are described with reference to oxazaphospholane (1) as the starting material, it should be understood that the following products may be obtained from the source of oxazaphospholane (1) being the corresponding sphingoid (2), thereby not necessitating the isolation of oxazaphospholane (1) during the processes.

According to one embodiment, oxazaphospholane (1) or (1a) is used for the manufacture of an acyclic oxazaphospholane derivative having the following formula (3):

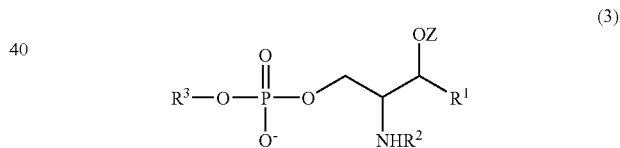
(3)

or its 2S, 3R stereoisomer, wherein $R^1$, $R^2$ and Z are as defined, and $R^3$ represent a hydrogen atom; an aliphatic moiety selected from aliphatic chain, amino aliphatic chain, heteroatom comprising aliphatic chain, aliphatic chain comprising a cyclic ring which ring may be saturated, partially saturated ring or an aryl group, said aliphatic chain may be branched or straight, saturated or unsaturated chain; or ether, polyether, or sugar moiety. According to this embodiment, the process comprises the step of reacting oxazaphospholane (1) with an alcohol of the formula $R^3OH$ where $R^3$ is as defined (although not a hydrogen atom), followed by treatment with an aqueous base or aqueous acid.

According to one embodiment, the alcohol of preference is selected from choline, N-protected ethanolamines, oligoethyleneglycol monoethers, polyethyleneglycol monoehthers, polyethers, or sugar moiety. Nonetheless, choline is one preferred embodiment.

The term "aqueous base" should be understood by those versed in the art as any organic or inorganic aqueous reagent known in the art of organic synthesis and capable of opening the cyclic phosphorous moiety, by cleaving the P—N bond therein, resulting in the acyclic oxazaphospholane derivate (3). Such reagents are known in the art and the following should be construed as a non-limiting list of such reagents: trialkylamine, alkali metal- or alkali earth metal-hydroxide, carbonate or bicarbonate. Specific aqueous bases include triethylamine, sodium carbonate, sodium bicarbonate, sodium hydroxide, potassium hydroxide.

The aqueous acid according to the invention may be any organic or inorganic acid known in the art of organic synthesis. Preferred acids are strong mineral acids and Lewis acids as known in the art. One particular example is HCl.

Oxazaphospholane (3) may be obtained in an unprotected from by reacting the compound with a suitable protecting group removing agent as known in the art [T. W Greene, P. G. M Wuts, Protective Groups in Organic Synthesis, Second Edition, (1980), John Wiley & Sons, Inc.]. The unprotected form of the 2S, 3R stereoisomer compound (3a) is shown the Scheme 1 hereinbelow as compound of formula (8a).

Oxazaphospholane (1) or (1a) wherein $R^1$, and Z are as defined and $R^2$ is a hydrogen atom may also be used for the manufacture of an acyclic oxazaphospholane derivative having the following formula (4):

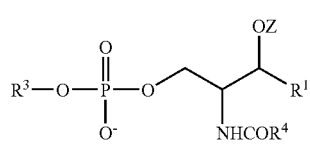

(4)

or its corresponding 2S, 3R stereoisomer (4a), wherein $R^3$ represent a hydrogen atom; an aliphatic moiety selected from aliphatic chain, amino aliphatic chain, heteroatom comprising aliphatic chain, aliphatic chain comprising a cyclic ring which ring may be saturated, partially saturated or aromatic ring, said aliphatic chain may be branched or straight, saturated or unsaturated chain; or an ether, polyether, or sugar moiety; and $R^4$ is hydrophobic group. According to this aspect, the process comprises reacting oxazaphospholane (3) with an acyl compound of formula $R^4C(O)Q$, wherein Q is a leaving group, as defined herein with respect to X, and may be the same or different from X.

According to one embodiment, $R^4$ represents a $C_1$-$C_{24}$ aliphatic moiety selected from saturated or unsaturated, branched or linear aliphatic chain, said aliphatic chain optionally containing an aliphatic ring; the aliphatic chain or ring optionally substituted with one or more substituents containing a heteroatom selected from oxygen, halogen, nitrogen and sulfur. One specific embodiment concerns $R^4$ representing a saturated or unsaturated $C_8$-$C_{24}$ aliphatic chain.

Oxazaphospholane (1) may also be used for the preparation of sphingomyelin and sphingomyelin analogues of formula (5) or its corresponding 2S, 3R stereoisomer (5a).

Thus, the invention concerns any synthetic sphingomyelin of formula (5) or (5a) as defined herein, excluding those previously described by Bruzik et al. [Bruzik, K. S. *J. Chem. Soc., Perkin Trans.* 1: 423-431, 1988] or in U.S. Pat. No. 5,220,043. specific sphingomyelin excluded by the present invention are those in which when $R^2$ represents a palmitoyl or stearoyl group, $R^1$ cannot represent trans-CH═CHC$_{13}$H$_{27}$ and $R^3$ cannot represent $CH_2CH_2N^+(CH_3)_3$.

The synthetic sphingomyelin and analogues thereof obtainable by the synthetic process according to the invention may have numerous applications. As indicated hereinbefore, sphingomyelin and sphingomyelin analogues are excellent candidates for drug delivery formulations based on liposomes and other lipid assemblies as well as inducing reverse cholesterol transport in cardiovascular diseases. The person skilled in the art will recognize the pharmacological and biochemical potential of the sphingomyelin and sphingomyelin analogues according to the invention and how they can be used in the medicinal and pharmaceutical industry. One specific example for the use of sphingomyelins according to the invention and the intermediates thereof is in the preparation of liposomes.

Currently available procedures which make use of 3-O— and N-protected sphingoid bases involve three protection-deprotection steps accompanied by the isolation and purification of the intermediates obtained. A one-pot procedure has now been developed and is disclosed herein.

According to this aspect a sphingomyelin of formula (5) is prepared from Oxazaphospholane (1) in which $R^2$ is a hydrogen atom and $R^1$, $R^3$ and $R^4$ are as defined above.

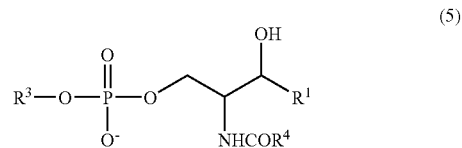

(5)

The process comprises reacting oxazaphospholane (4) with a protecting group removing agent to obtain a said sphingomyelin or sphingomyelin derivative.

The term "protecting group removing agent" should be understood in the art of organic synthesis as any agent capable of cleaving out the specific protecting group [T. W Greene, P. G. M Wuts, Protective Groups in Organic Synthesis, Second Edition, (1980), John Wiley & Sons, Inc.]. Some such agents include Tetrabutylammonium fluoride, Hydrogen fluoride, Borontrifluride etherate, strong acids as sulfuric acid, tosylic acid etc.

The invention also concerns the use of oxazaphospholane (1) or (1a) for the manufacture of an acyclic oxazaphospholane having the following formula (6):

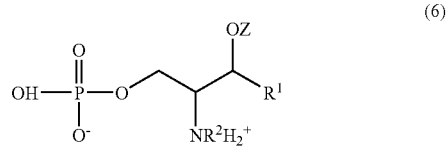

(6)

and its corresponding 2S, 3R stereoisomer (6a), wherein $R^1$, $R^2$ and Z are as defined. According to this aspect, the process comprises reacting oxazaphospholane (1) with an aqueous base or an aqueous acid as defined.

Oxazaphospholane (6) may be obtained in its unprotected form by reacting the compound with a suitable removing reagent [T. W Greene, P. G. M Wuts, Protective Groups in Organic Synthesis, Second Edition, (1980), John Wiley & Sons, Inc.]

Evidently, the invention concerns any oxazaphospholane, oxazaphospholane intermediates and sphingomyelin compounds and derivatives described herein, whenever obtained by the processes of the invention, either in the protected (i.e. including the Z substituent) or unprotected form. The term derivatives, which is used interchangeably with the term analogous denotes any compound within the scope of the general formulae provided herein which may be provided also by the synthetic procedures of the present invention.

The different processes of the invention may include one or more purification steps of the compounds thus obtained, or used in their crude form for further synthetic procedures, either those disclosed herein or other any other synthetic procedure which may make use of the compounds of the invention. According to one embodiment the purification may include filtration followed, if desired, by column chromatography on Silica gel using a proper eluent as known in the art.

The different processes disclosed herein are summarized in the following Scheme 1 (with respect to the 2S, 3R stereoisomer):

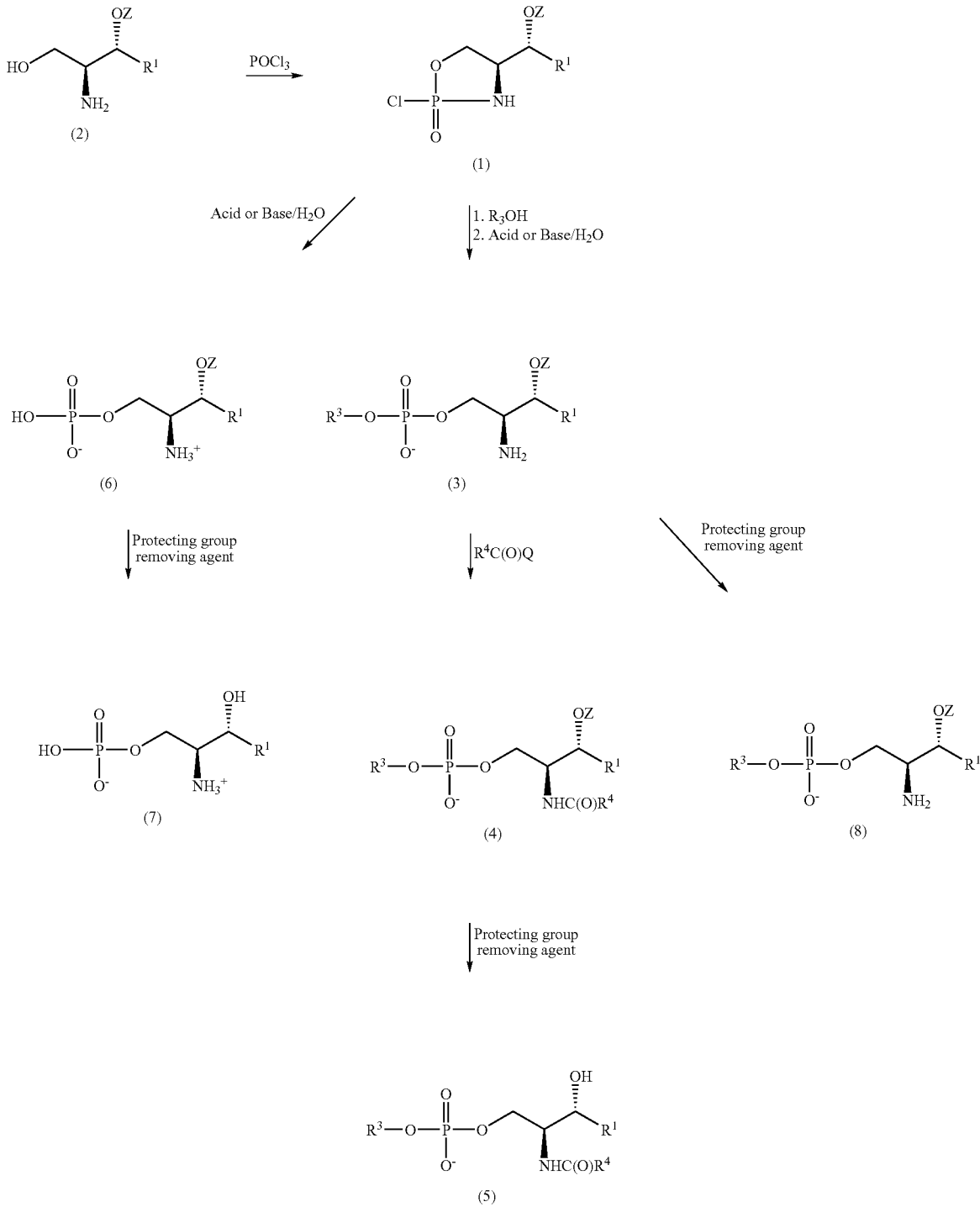

It should be noted that the starting material, sphingolipid (2) or its corresponding (2a) may be obtained by the process described in the following Scheme 2, using N-protected diolamine compound.

The process of preparing the protected sphingoid of formula (2a) is illustrated in the following Scheme 2:

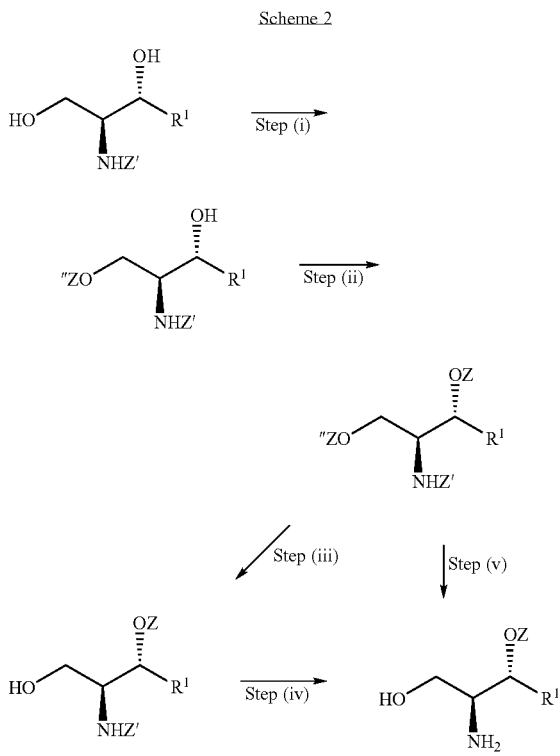

Scheme 2

According to the above scheme 2, the N-protected diolamine (Z' being the protecting group) is reacted with a selective primary alcohol protecting group Z" (step (i)) followed by protecting a secondary alcohol in the 3 position with a second protecting group Z (step (ii)), where Z, Z', and Z" being different protecting groups. Subsequently, selectively removing the primary protecting group Z" on the alcohol in position 1 (step iii) and the protecting group Z' on the amine in position 2 (step (iv)). The removal of Z" and Z' may be performed sequentially (steps (iii) and (iv)) or simultaneously (step (v)).

The invention will now be described by way of examples. While the foregoing description describes in detail only one specific embodiment of the invention, it will be understood by those skilled in the art that the invention is not limited thereto and that other sphingoid and phosphosphingoid compounds may be obtained, without departing from the scope of the invention as defined herein.

SPECIFIC EXAMPLES

Synthesis of 3-O-tert Butyldiphenylsilyl-D-erythro-sphingosine (2a)

N-tert-Butoxycarbamoyl-D-erythro-sphingosine (670 g, 1.67 mol) was dissolved in dry dichloromethane (12 L) and imidazole (284 g, 4.18 mol) and tert-Butyldimethylchlorosilane (277 g, 1.84 mol) were subsequently added. After stirring for 2.5 h at room temperature (RT) the reaction was completed and additional amounts of imidazole (114 g, 0.75 mol) and tert-Butyldiphenylchlorosilane (686 ml, 2.2 mol) were added. The reaction mixture was stirred for an additional period of 12 h followed by washing with water, evaporated and redissolved in EtOH (18 L).

To the redisolved solution concentrated aqueous HCl (4 L) was added and the solution was stirred for 2 h. The solution was then cooled and cold solution of $NH_4OH$ (3.5 L, 26%) was added for neutralization. The mixture was filtered, dried, evaporated and the residue was purified on Silica gel column, using the gradient $CHCl_3$: MeOH 95.5:0.5 to 97:3 as eluent.

Yield of 500 g (56% from the initial N-Boc-Sphingosine) of (2a) as yellowish oil was obtained.

$^1$H NMR 300 MHz (δ ppm, $CDCl_3$): 0.88 (t, 3H), 1.06 (s, 9H), 1.15 (bm, 4H), 1.26 (bs, 18H), 1.81 (bm, 5H), 2.80 (m, 1H), 3.435 (m, 1H), 3.61 (m, 1H), 4.015 (m, 1H), 5.28 (m, 2H), 7.37 (m, 6H), 7.65 (m, 4H)

Synthesis of (4S)-4-[(1R)-1-(tert-Butyldiphenylsilyloxy)-hexadec-2-enyl]-2-chloro-2-oxo-[1,3,2]-oxazaphospholidine (1a)

To a solution of $POCl_3$ (13 ml, 21.7 g, 142 mmol) in hexane (100 ml) a solution of triethylamine (40 ml, 29.1 g, 288 mmol) in dichloromethane (60 ml) was added at −10° C. with stirring. The solution thus obtained was cooled to −20° C. and a solution of 2a (50 g, 93 mmol) in dichloromethane (500 ml) was added. The solution of compound (1a) thus obtained was used as such for preparation of derivatives as described below.

Compound (1a) was isolated purified by evaporation to provide a yellow-brown oil thus obtained was subjected to mass-spectrum analysis. m/e=617 (m+).

Synthesis of 1-O-Phosphocholino-(2S,3R)-2-hexadecylamido-octadec-4-ene-1,3-diol (5a) (N-palmitoylsphingosyl phosphocholine, N-palmitoyl sphingomyelin)

To the solution comprising compound 1a a solution of choline tosylate salt (86 g, 312 mmol) in MeCN (1.5 L) was added followed by a solution of triethylamine (20 ml) in dichloromethane (30 ml) and the mixture was stirred at RT for 12 h. The reaction mixture was then concentrated, redissolved in THF (2.5 L), filtered and hydrolyzed with 11 ml of concentrated aqueous HCl. Then the solution was dried with $MgSO_4$ and reacted with palmitoyl chloride (31 ml, 28 g, 102 mmol) in the presence of excess of triethylamine. The solution was filtered, evaporated, redissolved in dichloromethane, washed several times with $MeOH/H_2O$, dried, evaporated and the residue was reacted with excess of tetrabutylammonium fluoride 1M solution in THF at 45° C.

After completion the solution was evaporated, the residue re-dissolved in dichloromethane, washed with $MeOH/H_2O$, concentrated and precipitated in acetone. The crude sphingomyelin thus obtained was filtered and purified by column chromatography on Silica gel using $CH_2Cl_2$:MeOH:$H_2O$ 65:25:4 as eluent to yield 20 g (31% from the sphingoid starting material 2a) of sphingomyelin 5a as white solid. $^1$H NMR 300 MHz (δ ppm, $CD_3OD$): 0.89 (t, 6H), 1.28 (bm, 44H), 1.37 (bm, 2H), 1.56 (bm, 2H), 2.015 (m, 2H), 2.17 (m, 2H), 3.21 (s, 9H), 3.62 (m, 2H), 3.90-4.12 (m, 4H), 4.26 (m, 2H), 5.435 (dd, 1H), 5.69 (dt, 1H)

Synthesis of 1-Phosphocholino-(2S,3R)-2-amino-octadec-4-ene-1,3,-diol (7a)

To a solution comprising compound 1a prepared starting from 7.4 gr. of compound 2a a solution of 12.7 gr. of choline tosylate in dry acetonitrile was added. A solution of 5.9 ml. of triethylamine in 4 ml. DCM was added thereto. The reaction mixture was stirred overnight. The reaction mixture was then concentrated, 250 ml. of hexane was added and evaporated to dryness. The residue was redissolved in 390 ml. of THF and precipitated choline tosylate was filtered. Concentrated HCl (1.7 ml) was added and the reaction mixture was stirred for 1 hour. The reaction mixture was dried over magnesium sulfate, filtered, and the pH was basified with triethylamine. The precipitation was filtered, the filtrate was evaporated to dryness and then redissolved in a solvent mixture consisting of chloroform, methanol and water (8:4:3). The lower phase was separated and washed 4 times with the same upper phase and evaporated.

The crude product was dissolved in 45 ml. of 1M tetrabutylammonium fluoride in THF and the reaction mixture was stirred at 45° C. for 2 hours. The resulting solution was evaporated and the crude product was purified by silicagel chromatographic column. (Eluent: gradual mounting concentration of methanol in chloroform).

The relevant fractions were evaporated and the resulting product was then co-evaporated with acetonitrile. 1.49 of pure product was obtained (23% yield).

$^1$H NMR 300 MHz (δ ppm, CD$_3$OD): 0.92 (t, 3H), 1.31 (bm, 20H), 1.44 (m, 2H), 2.10 (q, 2H), 2.92 (m, 1H), 3.33 (m, 1H), 3.67 (m, 2H), 3.92 (m, 1H), 4.04 (m, 2H), 4.30 (m, 2H), 5.55 (dd, 1H), 5.78 (dt, 1H).

Synthesis of (2S,3R)-2-amino-octadec-4-ene-1,3-diol-1-phosphate (8a)

A solution of compound 1a prepared from 8 gr. of compound 2a was dissolved in 400 ml. THF and 18 ml. of concentrated HCl was added. Reaction mixture was cooled to −20° C. and filtered. Ammonia solution (13 ml) was added in order to neutralize the reaction mixture and the substance obtained was evaporated. The residue obtained was evaporated to dryness, and the residue was dissolved in 400 ml. of a solvent mixture consisting of chloroform, methanol and water (8:4:3) and the lower phase was separated.

The organic phase was evaporated and was subjected to silicagel column using 20% methanol in chloroform as eluent. The relevant fractions were combined and evaporated; 2.5 gr. of (2S, 3R) 2-amino-octadec-4-ene-3-(t-butyl-dipenylsilyloxy)-1-ol-phosphate was obtained (27% yield).

The product obtained was suspended in 30 ml. THF, 4.4 ml of 1M THF solution of tetrabutylammonium fluoride was added thereto and the reaction was stirred at 45° C. for 2 hours. The reaction mixture was evaporated and the residue was purified on a silicagel chromatographic column using methanol chloroform mixture 1:1 as eluent.

The relevant fractions were combined and evaporated, triturated with acetonitrile, filtered and dried. 1.3 gr of product was obtained (23%) overall yield.

$^1$H NMR 300 MHz (δ ppm, CD$_3$COOD): 0.95 (t, 3H), 1.35 (bm, 21H), 1.44 (m, 2H), 2.12 (m, 2H), 2.21 (m, 1H), 3.74 (m, 1H), 4.31 (m, 2H), 4.55 (t, 1H), 5.61 (dd, 1H), 5.98 (dt, 1H).

The invention claimed is:

1. An oxazaphospholane compound of formula (1):

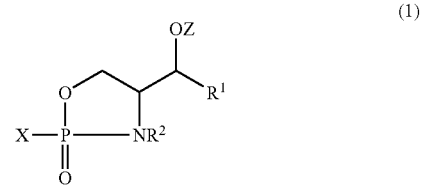

wherein
R$^1$ represents a C$_1$-C$_{24}$ aliphatic moiety which may be a saturated or unsaturated, branched or linear chain, optionally comprising an aliphatic ring,
R$^2$ represents a hydrogen atom or hydrophobic group, the hydrophobic group is a C$_1$-C$_{24}$ aliphatic moiety which is a saturated or unsaturated, branched or linear aliphatic chain, the aliphatic chain optionally comprising an aliphatic ring, the aliphatic chain or ring optionally substituted with one or more substituents comprising a heteroatom selected from the group consisting of oxygen, halogen, nitrogen and sulfur,
Z represents a protecting group selected from the group consisting of methoxymethyl (MOM), tetrahydropyranyl (THP), diphenylmethyl, triethylsilyl (TES), t-butyldimethylsilyl (TBDMS), mesitoate, 9-fluorenylmethyl carbonate (f-moc), t-butyl carbamate (t-boc), and Si(R$^5$)$_3$, R$^5$ may be the same or different in the same moiety and represent a C$_1$-C$_6$ branched or straight alkyl group or an aryl group, and
X represents a chemical moiety that is replaced under nucleophilic attack in the presence of a nucleophilic reagent and is selected from the group consisting of a halogen atom, borate, ethylene chlorophosphite, methyl phosphodichloridite, chloro-N,N-diisopropylaminomethyxophosphite, and [(isopropyl)2N]2POCH2CH2CN,
wherein X is optionally substituted with a group selected from the group consisting of an alcohol, an ether, a polyether and a sugar moiety,
wherein the alcohol contains an aliphatic moiety selected from the group consisting of an aliphatic chain, an amino aliphatic chain, a heteroatom comprising an aliphatic chain, an aliphatic chain comprising a cyclic ring which ring may be saturated or partially saturated and an aryl group, the aliphatic chain may be a branched or straight, saturated or unsaturated chain.

2. The oxazaphospholane compound of claim 1, wherein R$^1$ represents a C$_8$-C$_{24}$ aliphatic moiety.

3. The oxazaphospholane compound of claim 1, wherein R$^2$ represents a hydrogen atom or a saturated or unsaturated C$_8$-C$_{24}$ aliphatic moiety.

4. The oxazaphospholane compound of claim 3, wherein R$^2$ represents a hydrogen atom.

5. The oxazaphospholane compound of claim 1, wherein X represents a halogen atom.

6. The oxazaphospholane compound of claim 5, wherein X represents Cl.

7. The oxazaphospholane compound of claim 1, wherein Z represents a Si(R$^5$)$_3$ group in which R$^5$ may be the same or different in the same Si(—R$^5$)$_3$ group and represent a C$_1$-C$_6$ branched or straight alkyl group or an aryl group.

8. The oxazaphospholane compound of claim 1, wherein Z represents Si(Ph)$_2$(t-Bu).

9. An oxazaphospholane compound of frmula

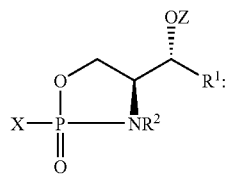
(1a)

(1a) being the 2S,3R stereoisomer of the compound of claim 1, wherein $R^1$, $R^2$, X and Z are as defined in the claim 1.

10. The oxazaphospholane compound of claim 1, wherein $R^1$ is (E)-CH=CHC$_{13}$H$_{27}$, $R^2$ is hydrogen, X is Cl and Z is Si(Ph)$_2$(t-Bu).

11. The oxazaphospholane compound of claim 1, wherein $R^1$ is (E)-CH=CHC$_{13}$H$_{27}$, $R^2$ is hydrogen, and X is substituted with the group —O—CH$_2$—CH$_2$—N$^+$(CH$_3$)$_3$.

12. The oxazaphospholane compound of claim 1, being the (E)-geometrical isomer of the compound of formula (1b):

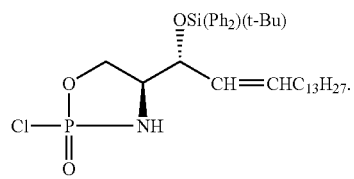
(1b)

13. The oxazaphospholane compound of claim 1, being an isolated stable compound.

14. A process for the manufacture of an oxazaphospholane compound of formula (1) as defined in claim 1, the process comprising reacting a phosphorylating reagent selected from the group consisting of POW$_3$, where W represents a halogen atom, an ethylene chlorophosphite, a methyl phosphodichloridite, a chloro-N,N-diisopropylaminomethyxophosphite and [(isopropyl)$_2$N]$_2$POCH$_2$CH$_2$CN with a 3-O-protected sphingoid compound of formula (2):

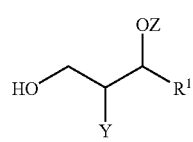
(2)

wherein $R^1$, Z and X are as defined in claim 1, and Y is an amine or an amino group.

15. The process of claim 14, further comprising reacting the phosphorylating reagent with a 2S, 3R stereoisomer of formula (2a):

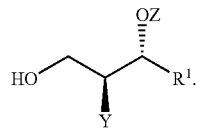
(2a)

16. The process of claim 14, wherein the phosphorylating reagent is reacted with the protected sphingoid compound in which Y represents NH$_2$.

17. The process of claim 14, wherein the phosphorylating reagent is POCl$_3$.

18. The process of claim 14, for the synthesis of the (E)-geometrical isomer of the compound of formula (1b):

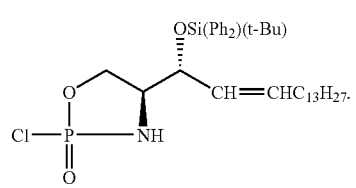
(1b)

19. An oxazaphospholane compound of formula (1):

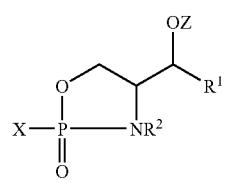
(1)

wherein $R^1$ represents a $C_1$-$C_{24}$ aliphatic moiety which may be a saturated or unsaturated, branched or linear chain, optionally comprising an aliphatic ring, $R^2$ represents a hydrogen atom or hydrophobic group, the hydrophobic group is a $C_1$-$C_{24}$ aliphatic moiety which is a saturated or unsaturated, branched or linear aliphatic chain, the aliphatic chain optionally comprising an aliphatic ring, the aliphatic chain or ring optionally substituted with one or more substituents comprising a heteroatom selected from the group consisting of oxygen, halogen, nitrogen and sulfur, Z represents a protecting group selected from the group consisting of methoxymethyl (MOM), tetrahydropyranyl (THP), diphenylmethyl, triethylsilyl (TES), t-butyldimethylsilyl (TBDMS), mesitoate, 9-fluorenylmethyl carbonate (f-moc), t-butyl carbamate (t-boc), and Si($R^5$)$_3$, $R^5$ being the same or different within the Si($R^5$)$_3$ and represent a $C_1$-$C_6$ branched or straight alkyl group, or an aryl group, and X represents a chemical moiety that is replaced under nucleophilic attack in the presence of a nucleophilic reagent, obtainable by the process of claim 14.

20. An oxazaphospholane compound of formula (1):

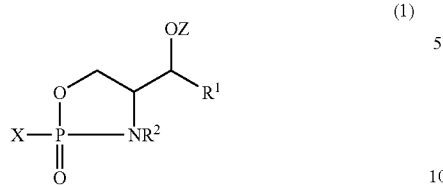

wherein
R$^1$ represents a C$_1$-C$_{24}$ aliphatic moiety which may be a saturated or unsaturated, branched or linear chain, optionally containing an aliphatic ring;
R$^2$ represents a hydrogen atom or hydrophobic group, the hydrophobic group is a C$_1$-C$_{24}$ aliphatic moiety selected from a saturated or unsaturated, branched or linear aliphatic chain, the aliphatic chain optionally containing an aliphatic ring, the aliphatic chain or ring optionally substituted with one or more substituents containing a heteroatom selected from the group consisting of oxygen, halogen, nitrogen and sulfur;
Z represents a protecting group selected from the group consisting of methoxymethyl (MOM), tetrahydropyranyl (THP), diphenylmethyl, triethylsilyl (TES), t-butyldimethylsilyl (TBDMS), mesitoate, 9-fluorenylmethyl carbonate (f-moc), t-butyl carbamate (t-boc), and Si(R$^5$)$_3$, wherein R$^5$ may be the same or different in the same moiety and is selected from a C$_1$-C$_6$ branched or straight alkyl group or an optionally substituted aryl group; and
X represents a leaving group selected from the group consisting of a halogen atom, borate, ethylene chlorophosphite, methyl phosphodichloridite, chloro-N,N-diisopropylaminomethyxophosphite, and [(isopropyl)$_2$N]$_2$POCH$_2$CH$_2$CN, wherein X is optionally substituted with a group selected from the group consisting of an alcohol, an ether, a polyether, and a sugar moiety, wherein the alcohol contains an aliphatic moiety selected from the group consisting of an aliphatic chain, an amino aliphatic chain, a heteroatom comprising an aliphatic chain, an aliphatic chain comprising a cyclic ring which ring may be saturated or partially saturated, and an aryl group, the aliphatic chain may be a branched or straight, saturated or unsaturated chain.

21. An oxazaphospholane compound of formula (1):

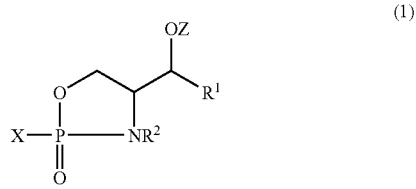

obtainable by the process of claim 14, wherein
R$^1$ represents a C$_1$-C$_{24}$ aliphatic moiety which may be a saturated or unsaturated, branched or linear chain, optionally containing an aliphatic ring;
R$^2$ represents a hydrogen atom or hydrophobic group, the hydrophobic group is a C$_1$-C$_{24}$ aliphatic moiety selected from a saturated or unsaturated, branched or linear aliphatic chain, the aliphatic chain optionally containing an aliphatic ring, the aliphatic chain or ring optionally substituted with one or more substituents containing a heteroatom selected from the group consisting of oxygen, halogen, nitrogen and sulfur;
Z represents a protecting group selected from the group consisting of methoxymethyl (MOM), tetrahydropyranyl (THP), diphenylmethyl, triethylsilyl (TES), t-butyldimethylsilyl (TBDMS), mesitoate, 9-fluorenylmethyl carbonate (f-moc), t-butyl carbamate (t-boc), and Si(R$^5$)$_3$, wherein R$^5$ may be the same or different in the same moiety and is selected from a C$_1$-C$_6$ branched or straight alkyl group or an optionally substituted aryl group; and
X represents a leaving group selected from the group consisting of a halogen atom, borate, ethylene chlorophosphite, methyl phosphodichloridite, chloro-N,N-diisopropylaminomethyxophosphite, and [(isopropyl)$_2$N]$_2$POCH$_2$CH$_2$CN, wherein X is optionally substituted with a group selected from the group consisting of an alcohol, an ether, a polyether, and a sugar moiety, wherein the alcohol contains an aliphatic moiety selected from the group consisting of an aliphatic chain, an amino aliphatic chain, a heteroatom comprising an aliphatic chain, an aliphatic chain comprising a cyclic ring which ring may be saturated or partially saturated, and an aryl group, the aliphatic chain may be a branched or straight, saturated or unsaturated chain.

22. The oxazaphospholane compound according to claim 21, wherein R$^1$ represents a C$_8$-C$_{24}$ aliphatic moiety; or Z represents a Si(R$^5$)$_3$ group in which R$^5$ may be the same or different in the same compound and represents a C$_1$-C$_6$ branched or straight alkyl group or an aryl group.

23. An oxazaphospholane compound of formula (1a):

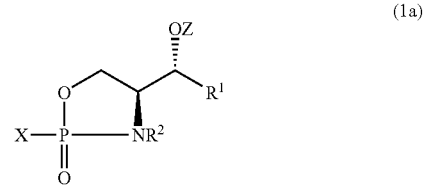

obtainable by the process of claim 14, wherein
R$^1$ represents a C$_1$-C$_{24}$ aliphatic moiety which may be a saturated or unsaturated, branched or linear chain, optionally containing an aliphatic ring;
R$^2$ represents a hydrogen atom or hydrophobic group, the hydrophobic group is a C$_1$-C$_{24}$ aliphatic moiety selected from a saturated or unsaturated, branched or linear aliphatic chain, the aliphatic chain optionally containing an aliphatic ring, the aliphatic chain or ring optionally substituted with one or more substituents containing a heteroatom selected from the group consisting of oxygen, halogen, nitrogen and sulfur;
Z represents a protecting group selected from the group consisting of methoxymethyl (MOM), tetrahydropyranyl (THP), diphenylmethyl, triethylsilyl (TES), t-butyldimethylsilyl (TBDMS), mesitoate, 9-fluorenylmethyl carbonate (f-moc) , t-butyl carbamate (t-boc), and Si(R$^5$)$_3$, wherein R$^5$ may be the same or different in the same moiety and is selected from a C$_1$-C$_6$ branched or straight alkyl group or an optionally substituted aryl group; and
X represents a leaving group selected from the group consisting of a halogen atom, borate, ethylene chlorophosphite, methyl phosphodichloridite, chloro-N,N-diisopropylaminomethyxophosphite, and [(isopropyl)$_2$N]$_2$POCH$_2$CH$_2$CN, wherein X is optionally substituted with a group selected from the group consisting of an alcohol, an ether, a polyether, and a sugar moiety, wherein the alcohol contains an aliphatic moiety selected from the group consisting of an aliphatic chain, an amino aliphatic chain, a heteroatom comprising an aliphatic chain, an aliphatic chain comprising a cyclic ring which ring may be saturated or partially saturated, and an aryl group, the aliphatic chain may be a branched or straight, saturated or unsaturated chain.

24. The oxazaphospholane compound according to claim 23, wherein

R$^1$ represents a C$_8$-C$_{24}$ aliphatic moiety, or

Z represents a Si(R$^5$)$_3$ group in which R$^5$ may be the same or different in the same compound and represents a C$_1$-C$_6$ branched or straight alkyl group or an aryl group.

* * * * *